United States Patent
McNeil et al.

[11] Patent Number: 5,171,229
[45] Date of Patent: Dec. 15, 1992

[54] NEEDLE TIP COVER

[76] Inventors: Michael B. McNeil, 934 N. Highland, Indianapolis, Ind. 46202; John D. Johnson, 283 N. Thorne St., Wabash, Ind. 46992; Kimberly M. McNeil, 317 Lanipo Dr., Kailua, Hi. 96734; David B. McLaren, 317 Lanipo Dr., Kailua, Hi. 96734

[21] Appl. No.: 685,042
[22] Filed: Apr. 15, 1991
[51] Int. Cl.⁵ .............................................. A61M 5/32
[52] U.S. Cl. .................................. 604/192; 604/110; 604/263
[58] Field of Search ............... 604/192, 197, 198, 263, 604/283, 905, 167, 180, 110

[56] References Cited

U.S. PATENT DOCUMENTS

| | | | |
|---|---|---|---|
| 3,904,033 | 9/1975 | Haerr | 604/263 |
| 4,006,744 | 2/1977 | Steer | 604/283 |
| 4,405,312 | 9/1983 | Gross et al. | 604/283 |
| 4,702,736 | 10/1987 | Kalt et al. | 604/180 |
| 4,723,948 | 2/1988 | Clark et al. | 604/283 |
| 4,801,296 | 1/1989 | Vaillancourt | 604/905 |
| 4,929,241 | 5/1990 | Kulli | 604/192 |
| 4,935,011 | 6/1990 | Hogan | 604/263 |
| 5,053,017 | 10/1991 | Chamuel | 604/263 |

FOREIGN PATENT DOCUMENTS 0183396  6/1986  European Pat. Off. ............ 604/283

*Primary Examiner*—C. Fred Rosenbaum
*Assistant Examiner*—Ronald Stright

[57] ABSTRACT

A small needle tip cover is provided which is capable of rendering a used disposable needle safe from accidental punctures. The needle tip cover can take the form of a small rectangular piece of sheet metal that is bent back upon itself. The bend is shaped to provide a spring means which is operable to force the opposing sides of the cover together. The inner surfce of each side includes a plurality of serrated burrs which contact the shaft of a used needle and prevent the tip thereof from escaping. The needle tip cover is kept open by a collapsible column. Until the introduction of a used needle tip therebetween, the column is subject to failure from any slight transverse force, such as that provided by the shaft of the needle pressing there against.

18 Claims, 6 Drawing Sheets

NEEDLE TIP COVER

FIELD OF THE INVENTION

This invention relates generally to devices for used disposable needles which render the needle safe from accidental puncture. In particular, this invention relates to covers for used disposable needles, and a method for attaching said covers on the tip of a used disposable needle.

BACKGROUND OF THE INVENTION

Medical personnel throughout the world confront the daily risk of accidental puncture by used disposable needles. In turn, accidental puncture presents the risk of infection by potentially deadly diseases. Over time, the exposure of doctors or veterinarians, nurses, and technicians to used needles is so massive that occasional punctures are almost a certainty. The medical industry is in dire need of a device that can eliminate these risks. But in order to be accepted, any such device must present a per item cost proportional to the risk present, and the device must be introducable into the medical industry without the need to alter the design of disposable needle assemblies themselves. Unless these two prerequisites are met, the device will likely be destined for the dust bin of history.

What is needed is a simply manufactured device that is extremely inexpensive and provides a method of rendering used disposable needles relatively safe from accidental punctures.

SUMMARY OF THE INVENTION

A needle tip cover comprising a first arm and a second arm is provided. A spring means is integrally formed to the two arms and is operable to force the two arms in opposing directions. The opposing arms include a plurality of serrated burrs which contact the shaft of a used disposable needle situated between the arms in such a way that the tip of the needle is covered and unable to escape.

In another embodiment, a needle tip cover comprising a resiliently closable shell is provided. The shell is capable of defining a first open shape which allows a used disposable needle tip to be transversely placed within the shell. After the needle tip is received within the shell, the shell tends to resiliently assume a second closed shape. The shell is provided with a means for preventing the escape of the needle tip when the shell has resiliently assumed its second closed shape. The means for preventing the escape of the needle tip can comprise a pliable surface, either integrally formed with or supported by, the shell which grips the needle and prevents movement thereof.

A method of using the above invention is also disclosed. The method comprises a first step of providing a needle tip cover which is capable of assuming a first open shape but tending to resiliently assume a second closed shape. The second step is accomplished by providing a means for opening the needle tip cover to assume its first open shape. Next, the shaft of the disposable needle is placed within the open needle tip cover in a motion which is substantially transverse to an axis defined by the needle. Finally, the means for opening the needle tip cover is disabled thereby allowing the needle tip cover to resiliently assume its second closed shape over the needle tip.

It is an object of the present invention to provide an improved device and method for rendering used disposable needles safe from accidental puncture. Other objects will become clear from the foregoing description.

DETAILED DESCRIPTION

Figure 2:
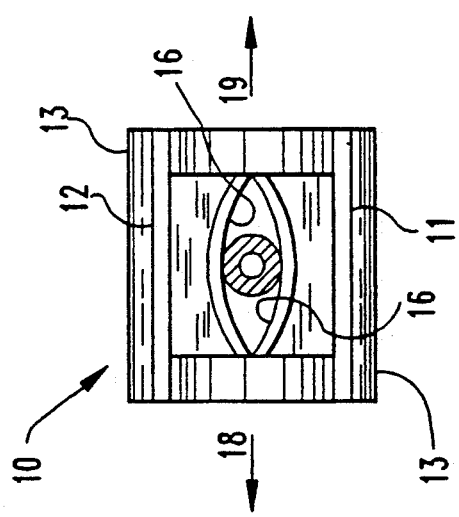
FIG. 2 is a view along the shaft of a needle showing the needle tip cover of FIG. 1.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
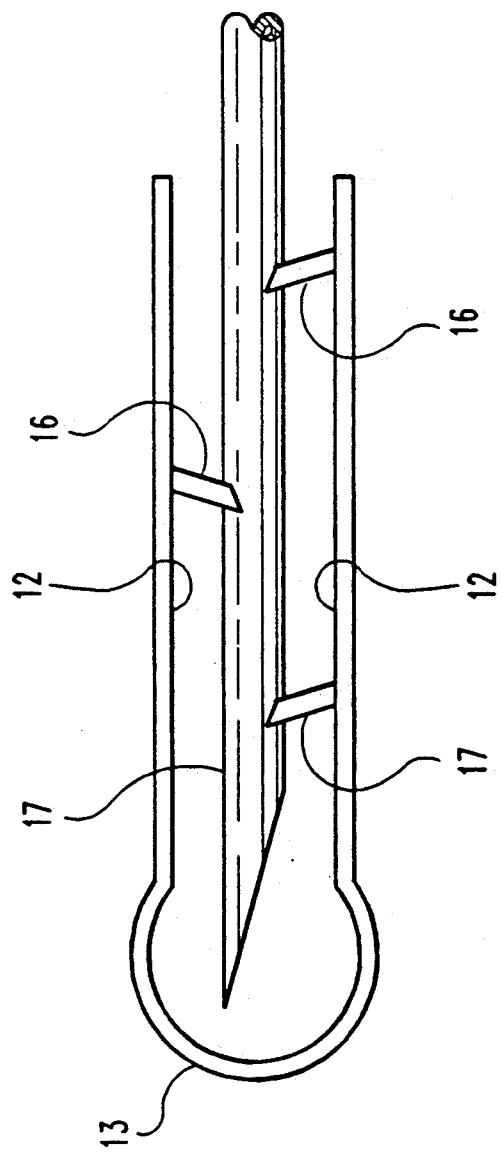
FIG. 1 is a side view of a needle tip cover according to a preferred embodiment of the present invention attached to the tip of a used disposable needle.

Referring now to FIG. 1, there is shown a needle tip cover 10 according to the preferred embodiment of the present invention, providing a protective cover for the tip of a used disposable needle 7. The tip cover 10 is preferably formed from a single piece of sheet metal, but could equally well be made out of some other substantially rigid material such as molded or extruded plastic. Cover 10 includes a first arm 11 integrally formed with a spring means 13, which in turn is integrally formed with arm 12. In this embodiment, spring means 13 is simply a sheet metal bend that tends to force arms 11 and 12 in opposing directions. As used in this patent, spring means is any resilient structure which operates to force two supported surfaces in opposing directions. As used in this patent, arm is defined as any substantially rigid structure which is capable of covering the tip of a used disposable needle.

In order to prevent needle tip 7 from escaping from between arms 11 and 12, there is provided burrs 14 and 15 which act in opposition to burr 16. As used in this patent, burr is defined as any rigid sharp edge that projects away from a supported surface. Burrs 14, 15 and 16 press against the shaft 17 of needle 7 preventing the needle from either advancing or retreating with respect to cover 10.

FIG. 2 shows the needle tip cover of FIG. 1 looking axially along the needle shaft. In this embodiment, burrs 15 and 16 are curved toward the center of cover 10. The curvature of burrs 15 and 16 prevents the needle from escaping from between arms 11 and 12 in either direction 18 or 19. Burrs having an infinite number of other shapes would work equally well in preventing the needle shaft from escaping. These shapes include but are not limited to serrated or multiple curve patterns.

Figure 3:
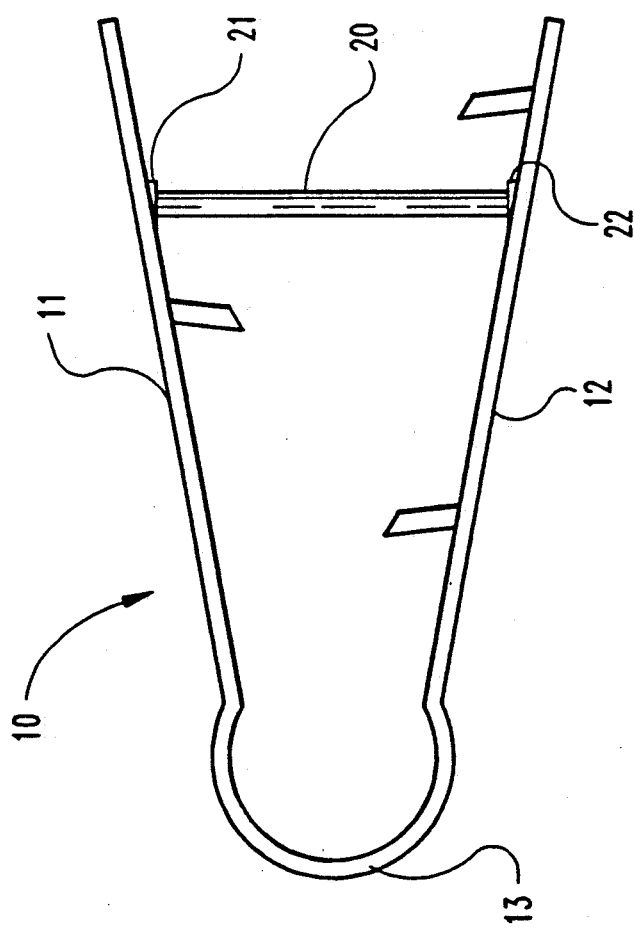
FIG. 3 is a top view of the needle tip cover of FIG. 1 held open by a collapsible column.

FIG. 3 shows the needle tip cover of FIG. 1 when arms 11 and 12 are being held apart by column 20. Arms 11 and 12 include column supports 21 and 22 respectively. Supports 21 and 22 are shaped so that forces acting on the column 20 are substantially axial. Column 20 is preferably formed in the shape of a thin walled tube which is capable of supporting a substantial axial load but which is subject to immediate collapse upon the application of a slight transverse force, such as that provided by the shaft of a needle striking said column.

Figure 4:
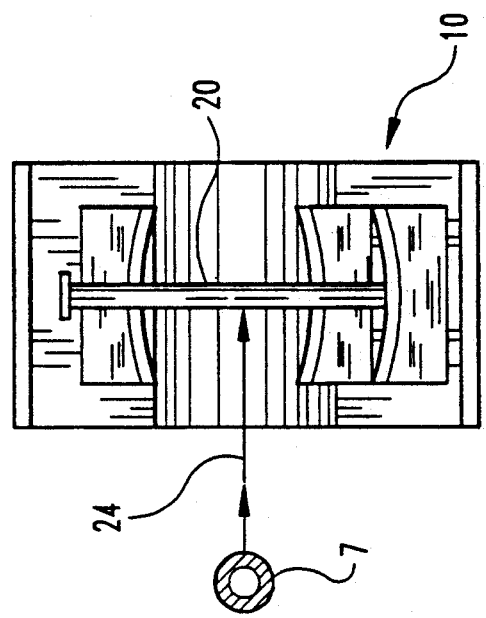
FIG. 4 is a view along the shaft of a needle when the cover is held open and the needle is approaching the collapsible column.

FIG. 4 shows the needle moving in direction 24 toward the column 20. FIG. 2 shows the cover 10 immediately after the needle 7 has struck the column 20 causing it to collapse. There are numerous other ways in which the arms 11 and 12 could be held apart until a needle tip is brought therebetween. These include but are not limited to providing a specialized dispenser for the tip covers or providing other collapsible support structures which automatically collapse when a needle tip is brought between the arms.

Figure 11:
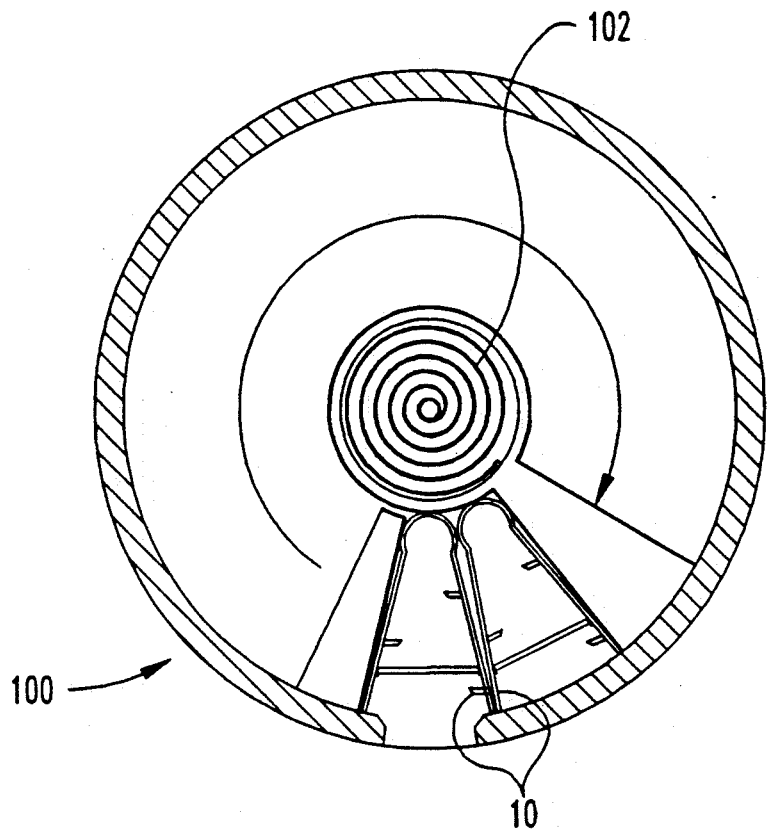
FIG. 11 shows a sectioned view of a dispenser for the needle tip covers shown in FIGS. 1-4.
Figure 12:
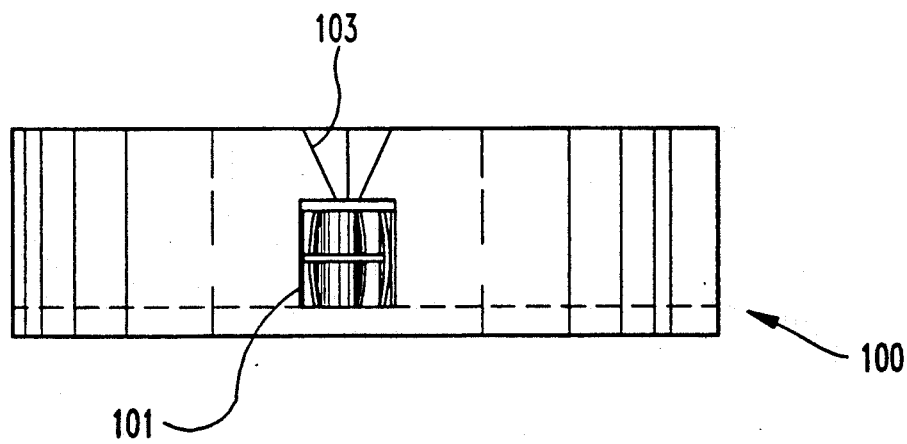
FIG. 12 is a side view of the dispenser shown in FIG. 11.

Medical personnel who are charged with removing a disposable needle from a patient can position a single tip cover, or a dispenser containing many clips, within arms reach of the location from where the needle is to be removed. Presumably, a dispenser could be provided which is small enough to be carried by medical personnel in their pockets throughout the work day. FIG. 11 shows a sectioned view of a possible dispenser 100 for the needle tip covers shown in FIGS. 1-4, which is small enough to be carried in a pocket. Dispenser 100 carries a plurality of covers 10 placed side by side around the periphery of the dispenser. Each tme a needle tip is covered, a needle tip cover 10 is removed from dispenser 100 via hole 101. When a cover is removed, spring 102 advances the covers to reveal a new cover 10 in front of hole 101. FIG. 12 shows a side view of dispenser 100. Needle tip covers 10 are removed from dispenser 100 one at a time through hole 101. Dispenser 100 also includes a guide means 103 that guides the tip of the used disposable needle to the appropriate position within the next available needle tip cover.

Figure 5:
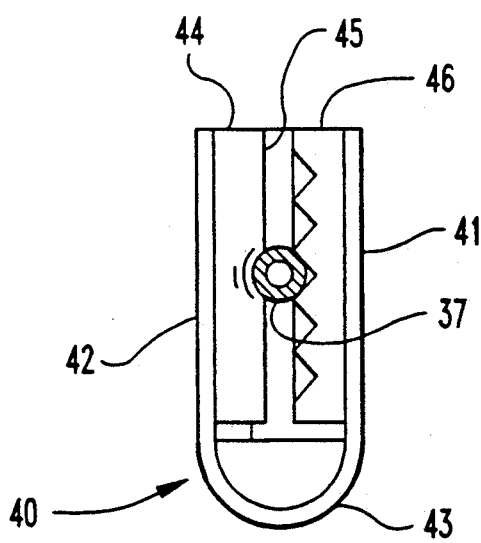
FIG. 5 is a view along the shaft of a needle showing another embodiment of the present invention.

FIG. 5 shows needle tip cover 40 according to another embodiment of the present invention. Cover 40 is shown after needle 37 has been trapped between arms 41 and 42. Arm 41 includes serrated burr 46 which may be integrally formed thereon. Burr 46 presses needle 37 against pliable surface 44 which in this case is attached to arm 42, but could equally be integrally formed thereon. Pliable surface 44 is preferrably made of a material, such as smooth rubber or plastic, that presents a relatively high coefficient of static friction with respect to a needle shaft pressed thereagainst. Like the embodiment described earlier, spring means 43 acts to force arms 41 and 42 toward each other. Pliable surface 44 could include a thin adhesive layer 45 thereon in order to further increase the coefficient of static friction between the layer 44 and needle 37.

Figure 6:
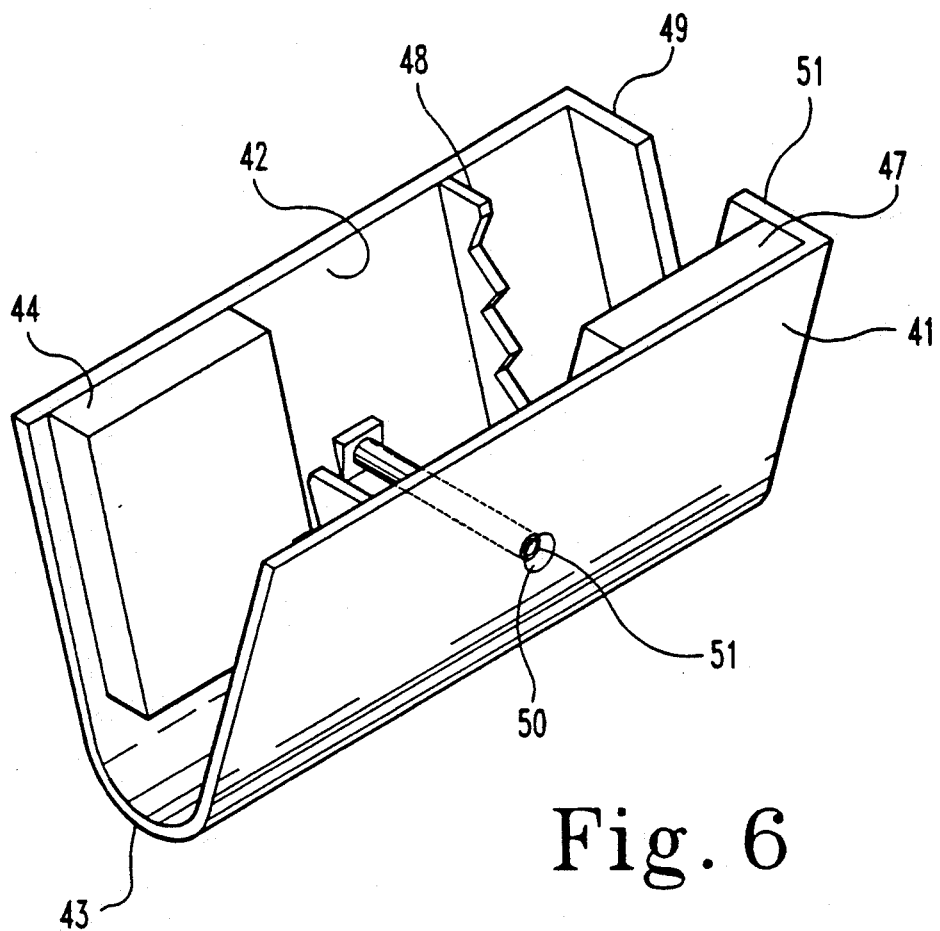
FIG. 6 is an isometric view of the needle tip cover of FIG. 5 shown held open.

FIG. 6 shows an isometric view of the needle tip cover 40 shown in FIG. 5. Cover 40 is shown being held open by column 60, which is wedged between arms 41 and 42. In this embodiment, arm 41 includes a bore 50 which is sized to allow column 60 to escape therethrough. A portion of end 51 of column 60 rests against the rim of bore 50. Column 50 is dislodged from the location shown when the shaft of a needle strikes the column 50 in a downward motion. When the column 60 is dislodged, said column escapes through bore 50 allowing arms 41 and 42 to collapse inward on the needle, as shown in FIG. 5. Cover 40 could equally well be held open by a collapsible column as previously described. In which case, the column would collapse upon the application of a slight transverse force. This slight force can be provided by striking the shaft of a used disposable needle against the column.

Figure 7:
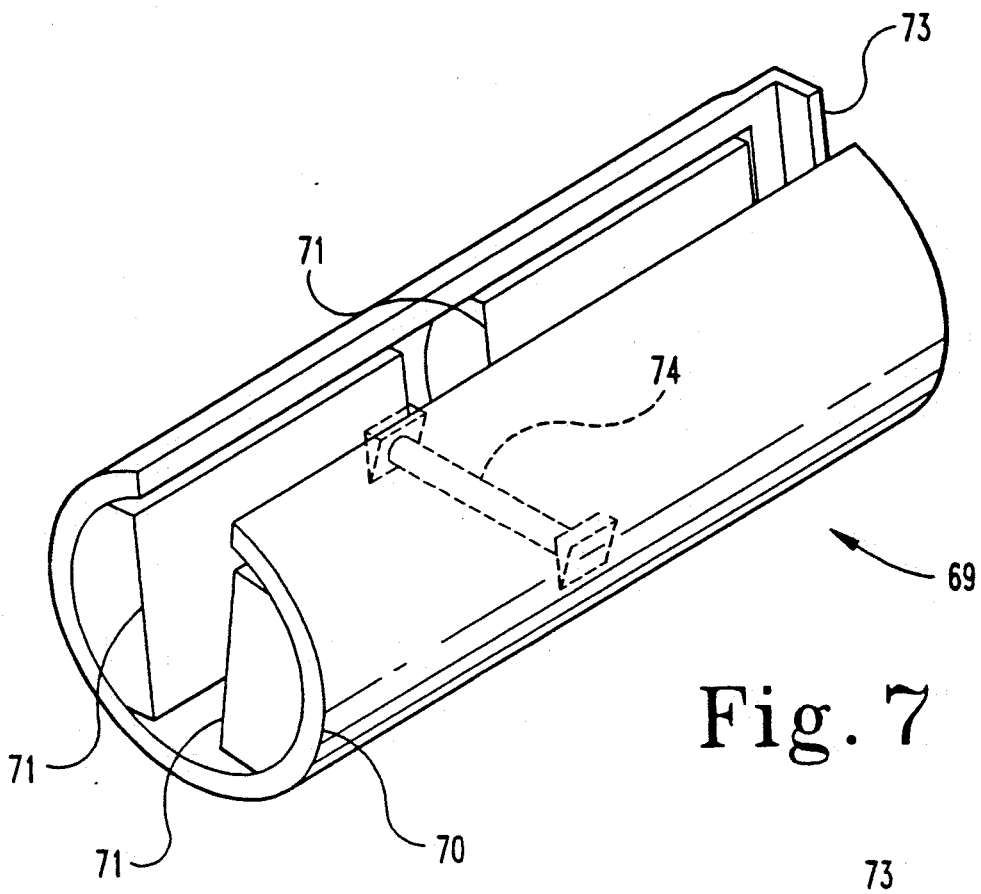
FIG. 7 is an isometric view of still another embodiment of the needle tip cover shown held open.
Figure 8:
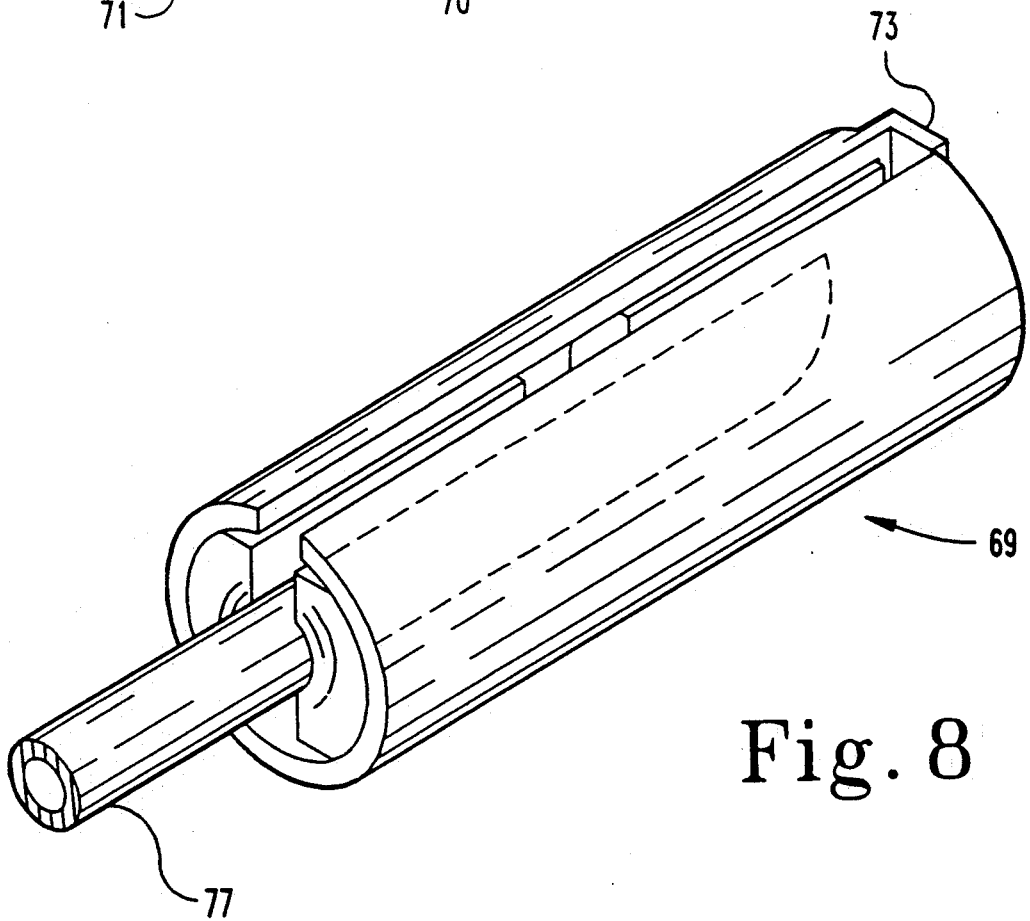
FIG. 8 is an isometric view of the needl tip cover of FIG. 7 shown after resiliently closing on a used disposable needle tip.

FIGS. 7 and 8 show still another embodiment of the present invention when the needle tip cover 69 is in a first open shape and after it has resiliently assumed a second closed shape. The needle tip cover 69 comprises a resiliently closable shell 70 which supports a pliable surface 71. Surface 71 provides a surface that will present a relatively high coefficient of static friction with respect to a needle shaft pressed thereagainst. Surface 71 might also include an adhesive thereon, or might simply be an appropriate surface integrally formed on the inner side of shell 70. Cover 69 also includes overlapping flanges 72 and 73 which either may be attached to or integrally formed on shell 70. In this case, needle tip cover 69 is held open by collapsible column 74. When the tip of a used disposable needle strikes column 74, the column buckles and collapses allowing shell 70 to resiliently assume its second closed shape, as shown in FIG. 8. When needle tip cover 69 closes on needle 77, pliable layer 71 presses along the shaft of needle 77 preventing the escape thereof. Overlapping flanges 72 and 73 are not necessary but can be provided to further prevent the tip of the needle from escaping.

Figure 10:
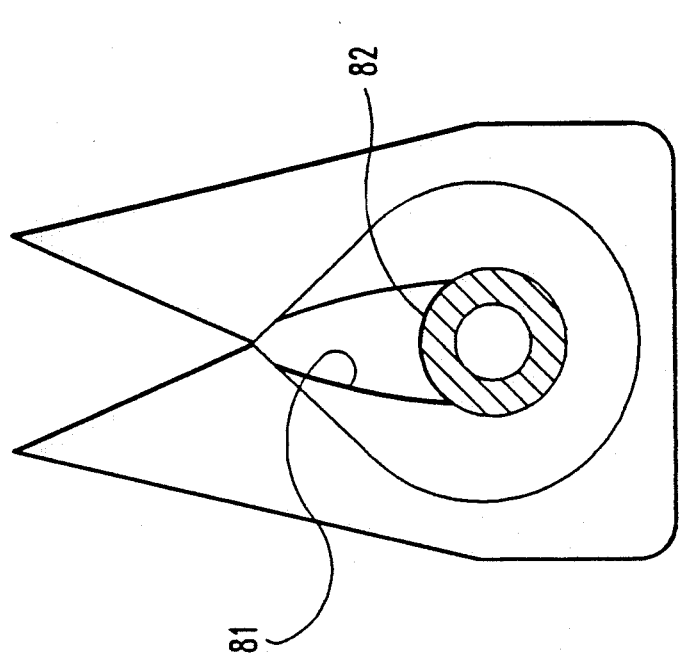
FIG. 10 is the needle tip cover of FIG. 9 shown after the needle tip cover has resiliently closed on a used disposable needle tip.
Figure 9:
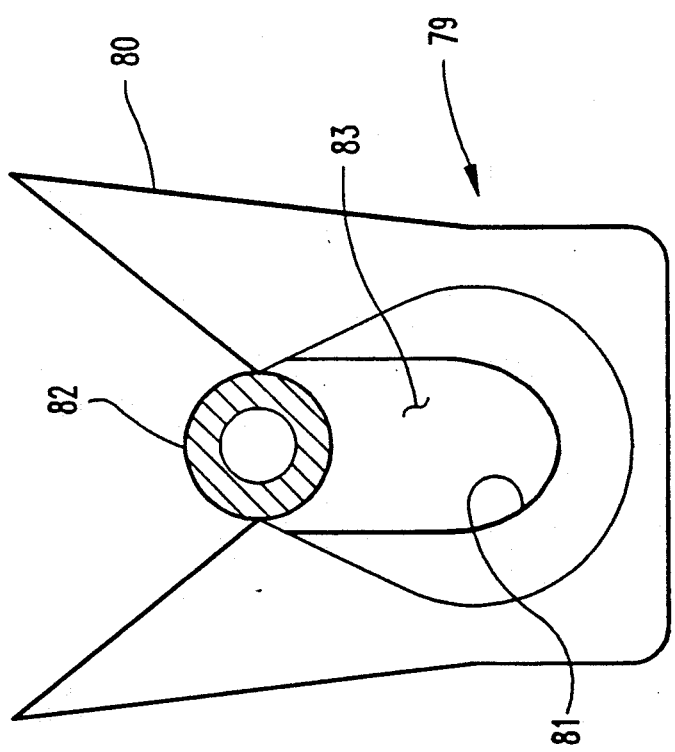
FIG. 9 is a view along the needle shaft showing still another embodiment of the present invention when the needle shaft itself is holding the cover open.

FIGS. 9 and 10 show end views of still another embodiment of the present invention, which could be formed from molded plastic. In this embodiment, the shaft of needle 82 forces the needle tip cover 79 to assume a first open shape. Needle tip cover 79 includes a resiliently closable shell 80 which defines a cavity 83 for receiving the tip and a portion of the shaft of needle 82 therein. Shell 80 supports a pliable surface 81, which could include an adhesive thereon or simbly be shaped to present a high coefficient of static friction, especially in the axial direction, to a needle pressed thereagainst. FIG. 10 shows the needle cover 79 after it has resiliently assumed its second closed shape. Pliable surface 81, which substantially surrounds needle 82, acts to prevent the needle from escaping from cover 79.

The needle tip cover shown in FIGS. 1-4 is similar to the embodiments shown in FIG. 7-10, in that arms 11 and 12 combined together with spring means 13 define a resiliently closable shell analogous to shell 70 or shell 80. FIGS. 3 and 4 show two different views of the needle tip cover 10 defining a first open shape, and FIGS. 1 and 2 show cover 10 after it has resiliently assumed a second closed shape. FIG. 3 further shows column 20 holding the shell defined by arms 11 and 12, and spring means 13, in the first open shape. FIG. 4 shows needle 7 moving to enter the shell in a motion having a direction 24 that is substantially transverse to an axis defined by the needle. The embodiment shown in FIGS. 5 and 6 likewise show a resiliently closable shell defining a closed shape covering a needle and a first open shape held open by column 60, respectively.

A method of rendering a used disposable needle safe from accidental puncture is also disclosed. The method comprises a first step of providing a needle tip cover which is capable of assuming a first open shape but tending to resiliently assume a second closed shape. The needle tip cover is positioned within arms reach of the location where the nurse is when he or she removes the disposable needle from the patient. Secondly, a means is provided for opening the needle tip cover to assume its first open shape. This means can be provided by the needle itself, as shown in FIG. 9, or can be provided by some structural support, such as the collapsible column 20 shown in FIG. 3, or possibly by some type of specialized dispenser. A unique third step is provided by placing the tip of a used disposable needle within the open needle tip cover in a motion which is substantially transverse to an axis defined by the needle. This step is shown in FIG. 4. The final step involves disabling the means for opening the needle tip cover in order to allow the needle tip cover to resiliently assume its second closed shape over the needle. This step can be accomplished by striking a collapsible column of the type shown in FIG. 3, or by simply passing the needle into the needle tip cover as shown in FIG. 10.

While the invention has been illustrated and described in detail in the drawings and foregoing description, the same is to be considered as illustrative and not restrictive in character. For instance, the needle tip covers shown could be made from formed sheet metal or molded plastic, and the means for preventing the escape of the needle tip from the cover could be any surface, either integrally formed on or attached to, the inner side of the cover, where the surface presents a sufficiently high coefficient of static friction with respect to the needle that the needle is unable to escape. It being understood that only the preferred embodiments have been shown and described and that all changes and modifications that come within the spirit of the invention are desired to be protected.

We claim:
1. a needle tip cover comprising:
a first arm;
a second arm;
spring means operable to force said arms together;
means acting against said spring means for holding said arms apart, said means comprising a collapsible column and being subject to being disabled by a transverse force applied thereagainst;
means adjacently between said first arm and said second arm for preventing a used disposable needle tip from escaping from between said arms.
2. The needle tip cover of claim 1 wherein:
said collapsible column includes a thin walled tubular portion.
3. The needle tip cover of claim 1 wherein:
said first arm is integrally formed with said spring means; and
said second arm is integrally formed with said spring means.
4. The needle tip cover of claim 3 wherein:
said means adjacently between said first arm and said second arm for preventing a used disposable needle tip from escaping includes at least one burr projecting out of at least one of said arms.
5. The needle tip cover of claim 3 wherein:
said means adjacently between said first arm and said second arm for preventing a used disposable needle tip from escaping includes a flange integrally formed on at least one of said arms.
6. The needle tip cover of claim 3 wherein:
said means adjacently between said first arm and said second arm for preventing a used disposable needle tip from escaping includes said second arm supporting a substantially pliable surface.
7. The needle tip cover of claim 5 wherein:
said substantially pliable surface includes an adhesive thereon.
8. A needle tip cover comprising:
a resiliently closable shell capable of being deformed into defining a first open shape but tending to resiliently assume a second closed shape;
whereby the tip of a used disposable needle can enter said shell in a motion that is substantially transverse to an axis defined by the needle when said shell is in said first open shape;
means within said shell for preventing the escape of the needle tip from within said shell when said shell has resiliently assumed said second closed shape; and
means for holding said shell in said first open shape, said means being disabled by the arrival of a used disposable needle tip within said shell.
9. The needle tip cover of claim 8 wherein:
said means within said shell for preventing the escape includes a pliable surface supported within said shell.
10. The needle tip cover of claim 8 wherein:
said shell includes an adhesive supported therein.
11. The needle tip cover of claim 8 wherein:
said means within said shell for preventing the escape includes a plurality of burrs projecting inward in said shell, said burrs contact the needle tip and prevent the movement thereof when said shell resiliently assumes said second closed shape.
12. The needle tip cover of claim 8 wherein:
said means for holding said shell in said first open shape includes a column that is capable of being dislodged.
13. The needle tip cover of claim 8 wherein:
said means for holding said shell in said first open shape includes a collapsible column lodged within said shell.
14. The needle tip cover of claim 13 wherein:
said collapsible column includes a thin walled tubular portion.
15. A method of rendering a used disposable needle safe from accidental puncture comprising the steps of:
a) providing a needle tip cover which is capable of assuming a first open shape but tending to resiliently assume a second closed shape;
b) providing means for opening said needle tip cover to assume said first open shape;
c) placing a used disposable needle tip within said needle tip cover in a motion which is substantially transverse to an axis defined by the needle; and
d) disabling said means for opening said needle tip cover, thereby allowing said needle tip cover to resiliently assume its second closed shape over the tip of the used disposable needle.
16. The method of claim 15 wherein:

the shaft of the used disposable needle pressing against said needle tip cover provides said means for opening said needle tip cover.

17. The method of claim 15 wherein:

said means for opening said needle tip cover is a column wedged within said needle tip cover.

18. The method of claim 17 wherein:

said step of disabling said means for opening said needle tip cover is accomplished by striking the needle against said column.

* * * * *